United States Patent [19]

Doran et al.

[11] Patent Number: 5,369,126

[45] Date of Patent: Nov. 29, 1994

[54] NONATETRAENOIC ACID DERIVATIVE FOR USE IN TREATING ACNE

[75] Inventors: Thomas I. Doran, West Orange; Michael Rosenberger, Caldwell; Stanley S. Shapiro, Livingston, all of N.J.

[73] Assignee: Hoffmann-La Roche Inc., Nutley, N.J.

[21] Appl. No.: 1,144

[22] Filed: Jan. 6, 1993

[51] Int. Cl.$^5$ .................. A61K 31/20; C07C 59/00
[52] U.S. Cl. ................................. 514/559; 554/218
[58] Field of Search ........................ 554/218; 514/559

[56] References Cited

U.S. PATENT DOCUMENTS 4,648,996  3/1987  Alig et al. .................. 525/420.5

OTHER PUBLICATIONS

Doran T., et al, Characterization of human sebaceous cell in vitro. J. Invest. Dermatol. 96: 341–348 (1991).

Farrell L., et al, The treatment of severe cystic acne with 13–cisretinoic acid. J. Amer. Acad. Dermatol. 3: 602–611 (1980).

Hammerstein J., et al, Use of cyproteron acetate in the treatment of acne, hirsutism and virilism. J. Steroid Biochem. 6: 827–836 (1975).

Karasek M., Isolation and characterization of cells from the human sebaceous gland. In Vitro 22: No. 3, Part II, p. 22a, abstract No. 46 (1986).

Knutson D., Ultrastructural observations in acne vulgaris. The normal sebaceous follicles and acne lesions. J. Invest. Dermatol. 62: 288–307 (1974).

Landthaler M., et al, Inhibitory effects of 13–cis–retinoic acid on human sebaceous glands. Arch. Dermatol. Res. 269: 297–309 (1980).

Lavker M., et al, Lamellar inlcusions in follicular horny cell: a new aspect of abnormal keratinization. J. Ultrastruc. Molec. Struct. Res: 69: 362–370 (1979).

Lavker M., et al, The relationship between bacteria and the abnormal fillcular keratinization in acne vulgaris, J. Invest. Dermatol. 77: 325–330 (1981).

Lyons F., et al, comparison of 13–cis–retinoic acid and cyproterone acetate on the clinical response, sebum secretion, dermal and epidermal lipogensis in acne. Br. J. Dermatol, 106: 728–734 (1982).

Mezick J., et al, Topical and systemic effects of retinoids on horn-filled urticulus size in the rhino mouse. A model to quantify "antikeratinizing" effects of retinoids. J. Invest. Dermatol. 83: 110–113 (1984).

Plewig G., et al, Hamster ear model for sebaceous glands. J. Invest. Dermatol. 68 171–176 (1977).

Plewig G., et al, Effects of two retinoids in animal experiements and after clinical application in acne patients: 13–cis–retinoic acid Ro 4–3780 and aromatic retinoid Ro 10″9359. In "Retinoids", CE Orfanos et al., ed., Springer-Verlag, pp. 219–235 (1981).

Rheinwald J., et al, Serial cultivation of strains of human epidermal keratinocytes: The formation of keratinizing colonies from single cells. Cell 6: 331–334 (1975).

Shapiro S., et al, Evaluation of Potential Therapeutic Entities for the Treatment of Acne. In Reichert U and Shoot B (eds): "Pharmacology of Retinoids in the Skin." Pharmacol. Skin, Basel, Karger, vol. 3, pp. 104–112 (1989).

(List continued on next page.)

Primary Examiner—José G. Dees
Assistant Examiner—Joseph M. Conrad, III
Attorney, Agent, or Firm—George M. Gould; William H. Epstein; Bruce A. Pokras

[57] ABSTRACT

A compound of the formula

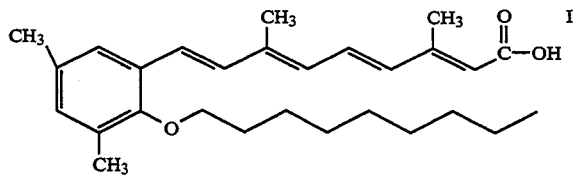

its pharmaceutically acceptable salts, and its pharmaceutically acceptable hydrolyzable esters for reducing sebum secretion and combatting acne as well as oral and topical compositions for use thereof.

8 Claims, No Drawings

OTHER PUBLICATIONS

Vane F., et al, Human biliary metabolites of isotretinoin: Identification, quantitation, synthesis, and biological activity. Xenobiotica 20: 193–207 (1990).

Weissman A., et al, Antiandrogenic effects of topically applied spironolactone on the hamster flank organ. Arch. Dermatol. 121: 57–62 (1985).

Wolff H., et al, Ulstrastructure of human sebaceous sollicles and comedones following treatment with vitamin A. Acta. Derm. Vener. Stockh., Suppl. 74, pp. 99–110 (1975).

NONATETRAENOIC ACID DERIVATIVE FOR USE IN TREATING ACNE

BACKGROUND OF THE INVENTION

Acne vulgaris is the most common skin disease in man and affects more than 80% of the population at various times. The etiology of acne is multifactorial, with excessive sebum secretion, hyperkeratinization and bacterial colonization playing key roles in its pathology.

The sebaceous gland is a holocrine gland which normally is found only in association with hair follicles (therefore the terminology pilosebaceous). The gland continuously forms the complex fatty mixture known as sebum, which finds passage up the hair follicle, through the production and eventual lysis of lipid-filled cells. The basal sebaceous cells, lining the edge of the gland, undergo division and create two daughter cells, one of which differentiates into a lipid-filled sebaceous cell. The lipid accumulation eventually results in lysis of the sebaceous cells. The liberated sebum is deposited onto the skin surface after migrating through the follicular (pilosebaceous) duct.

The pilosebaceous duct also plays a critical function in the development of acne. Obstruction of the pilosebaceous duct, caused by a hyperkeratinization and proliferation of the keratinocytes of the duct, may be the primary lesion in the development of acne (Lavker et al., 1981). Numerous studies have demonstrated that the entire pilosebaceous duct shows abnormal changes, which include an increased turnover of cells of the basal layer and the creation of an abnormal terminally differentiated stratum corneocyte, termed a "retention hyperkeratosis" (Knutson, 1974; Lavker and Leyden, 1979; Wolff et al., 1975).

The primary lesion of acne is the comedo. The open comedo (blackhead) consists of a firm mass of keratin and sebum which blocks and dilates the follicle pore. The upper portion of the blackhead is darkened by slow oxidative changes (not by dirt), and the lower portions are white. The closed comedo (whitehead), which is a collection of keratin and sebum with the follicular opening blocked, are potentially the starting point of deep inflammatory lesions.

It has been demonstrated that compounds which reduce sebum production reduce the severity of acne. Example of such compounds are 13-cis-retinoic acid, spironolactone and cyproterone acetate (Farrell et al., 1980; Hammerstein et al., 1975; Lyons et al., 1982; Weissman et al., 1985). It has also been shown that 13-cis-retinoic acid reduces the size of human sebaceous glands up to 90% (Landthaler et al., 1980). However, this compound can cause deleterious side effects such as hypervitaminosis A.

There are several standard in vitro and in vivo models known in the art for evaluating the anti-acne activity of compounds. For example, one in vitro model is the inhibition of the proliferation of cultured human sebaceous cells. (Shapiro et al., 1989, Vane et al., 1991).

The Syrian hamster ear provides a standard model for sebaceous gland activity which is predictive of the anti-acne activity of a compound. The ventral side of the earlobes of the Syrian hamster is richly endowed with sebaceous glands. These glands are large and are similar to human sebaceous glands since they have an infundibulum, a sebaceous duct, multiple lobules, and a pilary unit which enters from below the gland (Plewig and Luderschmidt, 1977). The turnover time is similar to that seen in man and the gland is androgen dependent. The Syrian hamster ear sebaceous gland is sensitive to 13-cis-retinoic acid (Plewig et al., 1981).

The rhino mouse model of antikeratinization is used as a standard model for comedolytic activity. In this mutant hairless mouse, the pilary canal widens, accumulates keratin, and is transformed into a keratin-filled utricle that resembles a human comedo. When retinoids which are active in this test are applied topically or given systemically, the utricle size decreases and returns to a near normal appearance resembling a normal pilosebaceous unit (Mezick et al., 1984). This model represents a method to determine antikeratinizing potency differences among biologically active agents and appears to be selective for retinoids which influence follicular keratinization and cell differentiation.

SUMMARY OF THE INVENTION

It has been discovered that the compound of the invention, (all-E)-3,7-dimethyl-9[3,5-dimethyl-2-(nonyloxy)-phenyl]-2,4,6,8-nonatetraenoic acid ("Compound I") which has the formula

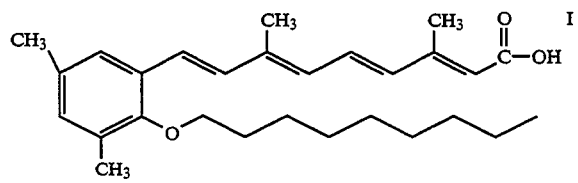

and its pharmaceutically acceptable salts and its pharmaceutically acceptable hydrolyzable esters, when administered either orally or topically, inhibits the proliferation of human sebocytes, reduces sebum secretion and inhibits utricle keratinization. Therefore, the administration of this compound provides a means for combatting diseases such as acne, oily hair and oily scalp. In such a manner, the administration of this compound may be used either as a prophylaxis against disorders such as acne or oily scalp and hair or in their treatment.

DETAILED DESCRIPTION OF THE INVENTION

The present invention comprises the compound (all-E)-3,7-dimethyl-9-[3,5-dimethyl-2-(nonyloxy)-phenyl]-2,4,6,8-nonatetraenoic acid which has the formula

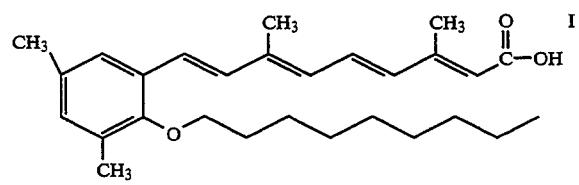

and its pharmaceutically acceptable salts and its pharmaceutically acceptable hydrolyzable esters.

The invention also comprises pharmaceutical compositions and methods of use of the compound of formula I, its pharmaceutically acceptable salts and its pharmaceutically acceptable hydrolyzable esters, to reduce sebum secretion and thus prevent or treat sebum-related disorders, such as acne, in persons to whom it is administered. It is known that inhibition of sebum production and/or secretion is an effective means of treating and- /or preventing disorders such as acne. Disorders caused by increased sebum secretion also include dermatological conditions such as seborrhea, including dandruff, oily skin, oily hair, whiteheads and blackheads.

In accordance with this invention, the topical and oral administration of the compound of formula I, its pharmaceutically acceptable salts and its pharmaceutically acceptable hydrolyzable esters, are effective in treating all forms of ache such as inflammatory and non-inflammatory.

The pharmaceutically acceptable salts includes any salt chemically permissible in the art for the compound of formula I and applicable to human patients in a pharmaceutically acceptable preparation. Any such conventional pharmaceutically acceptable salt of the compound of formula I can be utilized. Among the conventional salts which can be utilized are the base salts including, for example, alkali metal salts such as sodium or potassium, alkaline earth metal salts such as calcium or magnesium, and ammonium or alkyl ammonium salts.

In accordance with this invention the compound of formula I can be administered in the form of its pharmaceutically acceptable hydrolyzable esters. A hydrolyzable ester in accordance with the present invention is one which hydrolyzes under physiological conditions to yield the compound of formula I. Any pharmaceutically acceptable hydrolyzable ester of the compound of formula I can be used in the compositions and methods of this invention. Among such esters are the aromatic esters such as benzyl (OBzl) or benzyl substituted with lower alkyl, halo, nitro, thio, or substituted thio, i.e., lower alkyl, t-butyl, cyclopentyl, cyclohexyl, cycloheptyl, and 9-fluorenylmethyl.

The compound of formula I and its pharmaceutically acceptable salts and hydrolyzable esters may be prepared by any conventional means known in the art. For example, the compound of formula I and its pharmaceutically acceptable salts may be prepared by the means disclosed in Aig et al., U.S. Pat. No. 4,648,996 issued Mar. 10, 1987, the disclosure of which is hereby incorporated by reference. Pharmaceutically acceptable hydrolyzable esters of the compound of formula I may be prepared by conventional means from the compound of formula I by, for example, reaction of the compound of formula I with an alcohol.

In accordance with this invention, the aforementioned compound of formula I, or its pharmaceutically acceptable salts and its pharmaceutically acceptable hydrolyzable esters (collectively the "active ingredient of the invention"), can be provided as a means for reducing sebum secretion and acne lesions and thereby is useful as a prophylaxis or means for treating disorders such as acne by administering it in pharmaceutically acceptable oral or topical compositions and modes. These pharmaceutical compositions of the invention contain said active ingredient of the invention in association with a compatible pharmaceutically acceptable carrier material. Any conventional carrier material can be utilized. The carrier material can be an organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional form including: (a) a solid form for oral administration such as tablets, capsules, pills, powders, granules, and the like; and (b) preparations for topical administration such as solutions, suspensions, ointments, creams, gels, micronized powders, aerosols and the like. The pharmaceutical preparations may be sterilized and/or may contain adjuvants such as preservatives, stabilizers, wetting agents, emulsifiers, salts for varying the osmotic pressure, and/or buffers.

For topical administration to the skin the aforementioned composition is preferably prepared as ointments, tinctures, creams, gels, solutions, lotions, sprays, suspensions, shampoos, hair soaps, and the like. In fact, any conventional composition utilized for application to the scalp or skin can be utilized in accordance with this invention. Among the preferred methods of applying the composition containing the active ingredient of the invention is to apply the active ingredient of the invention in the form of a gel, lotion or cream. The pharmaceutical preparation for topical administration to the skin can be prepared by mixing the aforementioned active ingredient of the invention with non-toxic, therapeutically inert, solid or liquid carriers customarily used in such preparations. These preparations should contain at least about 0.01 percent by weight of the active ingredient of the invention based upon the total weight of the composition. Since the active ingredient of the invention is relatively non-toxic and non-irritating, it may be used in topical compositions in amounts exceeding 0.2% percent. It is preferred that these preparations contain about 0.01 to 0.2% percent by weight of the active ingredient of the invention based upon the total weight of the composition. It is also preferred to apply these preparations once or twice daily to the skin. These preparations can be applied according to the need of the patient. In carrying out this invention, the active ingredient of the invention can be applied in an aqueous solution or an alcohol solution such as ethyl alcohol.

In preparing the topical preparations described above additives such as preservatives, thickeners, perfumes and the like conventional in the art of pharmaceutical compounding of topical preparations can be used. In addition, conventional antioxidants can be incorporated into the topical preparations containing the aforementioned active agent of the invention. Among the conventional antioxidants which can be utilized in these preparations are included N-methyl-a-tocopherolamine, tocopherols, butylated hydroxyanisole, butylated hydroxytoluene, ethoxyquin and the like.

Conventional perfumes and lotions generally utilized in topical preparations for the hair can be utilized in accordance with this invention. Furthermore, if desired, conventional emulsifying agents can be utilized in the topical preparations of this invention.

Ointment formulations containing the active ingredient of the invention may comprise admixtures of a semisolid petroleum hydrocarbon with a solvent dispersion of the active ingredient of the invention.

Cream compositions containing the active ingredient of the invention preferably comprise emulsions formed from a water phase of a humectant, a viscosity stabilizer and water, an oil phase of fatty acid alcohol, a semisolid petroleum hydrocarbon and an emulsifying agent and a phase containing the active ingredient of the invention dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components are preferably derived from the reduction of a long-chain saturated fatty acid of at least about 14 carbon atoms. Cream-base pharmaceutical formulations containing the active ingredient of the invention may be composed of, for example, aqueous emulsions containing a fatty acid alcohol, semi-solid petroleum hydrocarbon, 1,2-ethyleneglycol and an emulsifying agent.

A preferred oral dosage form comprises tablets, capsules of hard or soft gelatin, methylcellulose or of another suitable material easily dissolved in the digestive tract. The oral dosages contemplated in accordance with the present invention will vary in accordance with the needs of the individual patient as determined by the prescribing physician. Generally, however, a daily dosage of from about 0.01 mg. to about 3 mg per Kg of body weight and preferably from about 0.025 mg to about 1.5 mg per Kg of body weight of the patient is utilized. This dosage may be administered according to any dosage schedule determined by the physician in accordance with the requirements of the patient.

It is likewise within the preview of the present invention to incorporate the active ingredient of the invention in any desired amount for enteral administration within the oral unit dosage form. It is preferred, however, to formulate preparations in such a manner that each dose form contains from about 1 mg to about 50 mg of the active ingredient of the invention with suitable therapeutically inert fillers and diluents. It is especially preferred to incorporate such a dosage into soft gelatin capsules and tablets.

In accordance with this invention, therefore the active ingredient of the invention, which shows a pronounced sebum suppressing and anti-acne activity, can thus be used in the pharmaceutical preparations mentioned above, for reducing sebum secretion and for the treatment of acne.

The dosage for treatment typically depends on the route of administration, the age, weight and acne condition of the individual.

EXAMPLE 1

The compound of formula I was prepared in accordance with the following scheme by the procedures described below:

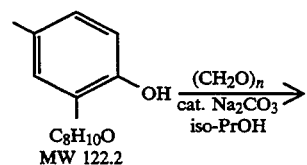

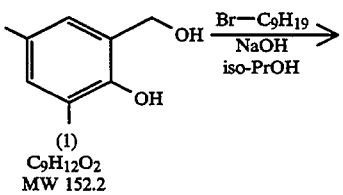

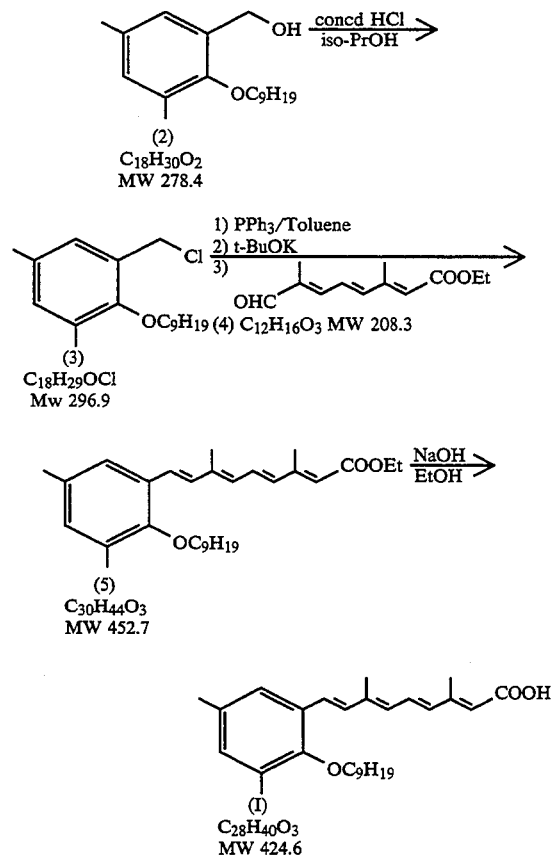

Step 1: Preparation of 2-Hydroxymethyl-4,6-dimethylphenol (1) M.W. 152.2

A 100-mL round-bottom flask equipped with a magnetic stirrer, condenser, and Ar-inlet tube was charged with 24.4 g (0.2 mol) of 2,4-dimethylphenol (Aldrich), 2.44 g of powder Na$_2$CO$_3$ (Baker), 7.8 g (0.26 mol) of paraformaldehyde (Aldrich), and 7.8 mL of isopropanol (Fisher). The mixture was stirred at 90°–100 °C. (bath temp.) for 5 hr. After cooling to room temperature, the mixture was poured into 200 mL of 1N NaOH (Fisher) and washed with 4×50 mL=200 mL of dichloromethane (Fisher). The combined dichloromethane washes were back-extracted with 20 mL of water. The combined aqueous layers were acidified with 20 mL of conc. HCl (Fisher) and extracted with 100 mL+25 mL=125 mL of dichloromethane (Fisher). The combined dichloromethane extracts were washed with 50 mL of brine, dried over Na$_2$SO$_4$, and concentrated to dryness at 50° C. under high vacuum to afford 22.0 g (72.4%) of crude (1) as a brown oil.

Step 2: Preparation of 2-(Nonyloxy)-3, 5-dimethylbenzene-methanol (2) M.W. 278.4

A 250-mL round-bottom flask equipped with a magnetic stirrer, condenser, and Ar-inlet tube was charged with 22.0 g (145 mmol) of crude (1), 24.7 mL (130 mmol) of 1-bromononane (Fluka), 5.79 (145 mmol) of sodium hydroxide (Fisher), and 100 mL of isopropanol (Fisher). After the mixture was refluxed overnight, 100 mL of water and 100 mL of hexane (Fisher) were added. The hexane layer was washed with 20 mL of 1N NaOH (Fisher). The combined aqueous layers were extracted with 50 mL of hexane. Then, the combined hexane solutions were extracted with 100 mL+2×50 mL=200 mL of 95% methanol. The combined methanol extracts were concentrated. The residual water was removed azeotropically with 100 mL of toluene. The residue was dried at 50° C. under high vacuum to give 28.1 g of crude (2) as a brown oil; 50.5% yield from (1), 77.7% yield based on 1-bromononane.

Step 3: Preparation of 1-(Chloromethyl)-3,5-dimethyl-2-(nonyloxy)benzene (3) M.W. 296.9

A 250-mL round-bottom flask equipped with a magnetic stirrer, condenser, and Ar-inlet tube was charged with 28.1 g (101 mmol) of (2), 28 mL of isopropanol (Fisher), and 42 mL of concd HCl (Fisher). After refluxing gently overnight, the mixture was cooled to room temperature and diluted with 140 mL of hexane (Fisher) and 140 mL of water. The organic layer was washed again with 140 mL of water. Then, the organic layer was washed with 4×50 mL=200 mL of 90% aq methanol. The hexane solution was dried over $Na_2SO_4$ and concentrated at room temperature under high vacuum to dryness to give 27.6 (92.3% yield) of (3) as a tan oil.

Step 4: Preparation of (All-E)-3,7-dimethyl-9-[3,5-dimethyl-2-(nonyloxy)-phenyl]-2,4,6,8-nonatetraenoic Acid Ethyl Ester (5) M.W. 452.7

A 500-mL flask equipped with a magnetic stirrer, condenser, and Ar-inlet tube was charged with 27.6 g (93.0 mmol) of (3), 21.9 g (83.7 mmol) of triphenylphosphine (0.9 equiv), and 93 mL of toluene (Fisher). After refluxing overnight, the mixture was cooled with an ice-water bath and the condenser was replaced by an addition funnel. Then, 74.4 mL (74.4 mmol) of 1.0M t-BuOH solution of t-BuOK (Aldrich) (0.8 equiv) was added over 15 min, and the resulting dark red suspension was stirred for 1 hr at room temperature. After cooling to −10° C., 15.5 g (74.4 mmol) of (4) (0.8 equiv) (dried under high vacuum prior to use) was added with the aid of 15 mL of toluene. The cooling-bath was removed and the mixture was stirred at room temperature for 3 hr.

[The aldehyde (4) is known in the art and may be prepared by any conventional means. An example of a general description for the preparation of (4) is contained in Bollag et al., U.S. Pat. No. 4,163,103, Jul. 31, 1979, the disclosure of which is hereby incorporated by reference]. (Note: In the following steps, the retinoids, especially their solutions, should be kept out of the light as much as possible!)

The reaction mixture was washed with 2×100 mL=200 mL of water. The combined aqueous layers were back-extracted with 50 mL of toluene. After drying over $Na_2SO_4$, the combined toluene solutions were concentrated to dryness at below 35° C. under high vacuum. The residue was redissolved in a mixture of 200 mL of hexane, 200 mL of methanol, and 20 mL of water. The methanol layer was back-extracted with 2×100 mL=200 mL of hexane. The combined hexane solution was concentrated to dryness at below 35° C. under high vacuum to give crude (5) as a red oil. This was dissolved in 100 mL of ethanol (Quantum Chemical). After cooling with an ice-water bath, a seed crystal of (5) was added. The resulting suspension was stored in a refrigerator overnight. The yellow precipitate was filtered and washed with 100 ml of cold 95% ethanol. Drying at room temperature under high vacuum gave 21.64 g of (5) as a yellow solid; 51.4% yield from the chloride (3) and 64.1% from the aldehyde (4).

Step 5: Preparation of (All-E)-3,7-dimethyl-9-[3,5-dimethyl-2-(nonyloxy)-phenyl]-2,4,6,8-nonatetraenoic Acid (I) M.W. 424.6

Note: The retinoids, especially their solutions, should be kept out of the light as much as possible!

A 500 mL round-bottom flask equipped with a magnetic stirrer, condenser, and Ar-inlet tube was charged with 21.6 g (47.8 mmol) of (5), 216 mL of ethanol (Quantum Chemical), and 19.1 mL (191 mmol) of 10N NaOH (Fisher). The mixture was refluxed for 20 min. After removal of the heater, the reaction flask was immersed in a water bath and 19.1 mL of acetic acid (Fisher) was added while the mixture was still warm. After cooling to room temperature, a seed crystal was added and the mixture was cooled with an ice-water bath. After stirring for 30 min, the resulting yellow suspension was stored in a refrigerator overnight. The yellow solid was filtered and washed with 100 mL of cold 90% aq EtOH. Drying under high vacuum gave 17.84 g of crude (I) as a yellow solid. This was suspended in 357 mL of ethanol. Then, 4.5 mL of conc. NH$_4$OH (Fisher, 29%) (ca. 1.5 equiv) was added. After dissolution, 4.5 mL of acetic acid (Fisher) was added. The resulting suspension was stored in a refrigerator overnight. The yellow solid was filtered, washed with 100 mL of cold 95% aq EtOH, and dried at room temperature under high vacuum overnight to give 15.3 of (I) (98.2% pure by HPLC analysis) as a yellow solid. This material was again suspended in 306 mL of ethanol. Then, 3.8 mL of conc. NH$_4$OH (Fisher, 29) (ca. 1.5 equiv) was added. After dissolution, 3.8 mL of acetic acid (Fisher) was added. The resulting suspension was stored in a refrigerator overnight. The yellow solid was filtered, washed with 100 mL of cold 95% aq EtOH, and dried at room temperature under high vacuum overnight to give 13.56 g of (I) (66.9% yield) as a yellow solid; 98.9% pure by HPLC analysis.

The overall yield from the aldehyde (4) was 42.9%. The overall yield from 2,4-dimethylphenol was 16.0%.

The compound of the invention was tested as described in Examples 2–4, below, in several acne models. It was non-toxic at all doses tested.

EXAMPLE 2

In Vitro Testing

Sebaceous cells are isolated from adult human sebaceous glands, derived from facial skin removed during cosmetic surgery, and cultured on a layer of mouse 3T3 fibroblasts (Rheinwald and Green, 1975). This method is based on that of Karasek (1986) and involves the selective removal of epidermal keratinocytes by an electrokeratome followed by the enzymatic and mechanical dissociation of sebaceous cells from the sebaceous glands (Doran et al., 1991).

The cells are cultured in Iscove's medium containing 10% fetal calf serum and 4 μg/ml dexamethasone.

Cells are plated in medium without the test compound and then given test compound in fresh medium 24–48 hours after the initial plating. The cultures are given fresh medium containing the test compound, every 48 hours. On the day of harvesting, the cultures are rinsed with 0.03% EDTA in PBS to remove only the 3T3 fibroblasts, followed by incubation in 0.05% trypsin/0.03% EDTA. The cells are suspended, mixed vigorously to prepare a single cell suspension and counted in a hemocytometer.

All test compounds are handled in the following manner. Stock solutions are made up as $10^{-2}$M solutions in DMSO and stored at $-20°$ C. in the dark. Solutions are never used after one month of storage. During experimental use, the solutions, which have been aliquoted, are brought to room temperature and used by diluting directly into complete medium to the appropriate concentration.

The compounds were tested for the inhibition of proliferation of sebaceous cell growth *in vitro* at the following concentrations: $10^{-6}$, $10^{-7}$, $10^{-8}$ and $10^{-9}$M. The results are shown below (Table 1) as the amount of compound necessary to inhibit the proliferation of sebaceous cells by 50% ($ED_{50}$) in $\mu$M as compared to a control culture which was treated only with diluent. These results demonstrate that the compound of the invention inhibits the proliferation of human sebocytes.

TABLE 1

| Inhibition of Human Sebocyte Proliferation In Vitro | |
| --- | --- |
| Compound | $ED_{50}$ ($\mu$M) |
| 13-cis retinoic acid | 0.05 |
| Compound I | 0.01 |

EXAMPLE 3

Hamster Ear Sebaceous Gland Assay

Charles River Golden Syrian male hamsters, weighing between 150 to 160 grams, were housed for one month after receipt before dosing with compounds. Hamsters were given the desired dose of either 13-cis retinoic acid or Compound I in propylene glycol for oral dosing studies. Compound I and 13-cis retinoic acid were stored at 4° C. protected from light. Fresh solutions were made up weekly.

Hamsters were given 0.2 ml of drug solution via oral intubation. Animals were dosed daily for five days, rested for two days, and dosed again for five days until 20 doses were given. Hamsters were weighed at the beginning and end of the dosing regimen.

Hamsters were sacrificed by $CO_2$ inhalation, and the ears removed for histological evaluation. One ear was fixed with 10% buffered formalin, processed for paraffin embedding, sectioned, and stained with hematoxylin and eosin (H&E). The area of sebaceous glands in cross-sections of hamster ears was examined by image analysis using a Leitz TAS Plus system.

Data is given as the average area of 30–40 sebaceous glands as percent of the control (solvent-treated) sections. The data is given in Table 2. These results demonstrate that the compound of the invention reduces the size of pre-existing hamster ear sebaceous glands when administered orally.

TABLE 2

| Effect of 4 Weeks Oral Dosing with Compound I on Hamster Ear Sebaceous Gland Size | | |
| --- | --- | --- |
| Dose (mg/kg) | Compound I % Decrease | 13-cis retinoic acid % Decrease |
| Experiment 1 | | |
| 0.5 | −19 | ND |
| 1.5 | −27 | ND |
| 5 | −33 | ND |
| Experiment 2 | | |
| 0.5 | −11 ns | −13 |
| 2.5 | −18 | −24 |
| 5 | −24 | −34 |
| 10 | −33 | −30 |
| Experiment 3 | | |
| a. vehicle = Propylene Glycol | | |
| 0.5 | −19 | ND |
| 1.6 | −27 | ND |
| 6 | −33 | ND |
| b. vehicle = Labrafil | | |
| 0.6 | −18 | ND |
| 1.6 | −26 | ND |
| 5 | −26 | ND |
| c. vehicle = Tween 80 | | |
| 0.5 | −13 | ND |
| 1.4 | −13 | ND |
| 6 | −22 | ND |

EXAMPLE 4

Rhino Mouse Utricle Assay

Male and female rhino mice were weighed prior to the start of an experiment. For topical studies, test compounds are dissolved in 100% acetone and 100 $\mu$l applied to the dorsa of the mice five times a week, once daily, for three weeks. For oral studies, test compounds were dissolved in 100% propylene glycol and 100 $\mu$l given by oral intubation 5 times a week, once daily, for three weeks. Final body weights were recorded at the time of sacrifice, done by $CO_2$ inhalation. A flap of skin from the dorsa was cut out and processed by histological methods to produce a whole mount of the tissue. Utricle size was measured by image analysis using either the Leitz TAS Plus system or the Ultimage system on a modified MACINTOSH computer. Data is given as the % change from solvent-treated control tissue (Tables 3 and 4). These results demonstrate that the compound of the invention reduces the size of rhino mouse utricles when administered topically or orally.

TABLE 3

| Effect of 3 Weeks Topical Dosing with Compound I on Rhino Mouse Utricle Size | | |
| --- | --- | --- |
| Dose (% Solution) | Compound I % Decrease | 13-cis retinoic acid % Decrease |
| Experiment 1 | | |
| 0.01 | −10 | −44 |
| 0.1 | −42 | −55 |
| Experiment 2 | | |
| 0.001 | −1 | −27 |
| 0.01 | −11 | −58 |
| 0.1 | −30 | −61 |

TABLE 4

| Effect of 3 Weeks of Oral Dosing with Compound I on Rhino Mouse Utricle Size | | |
| --- | --- | --- |
| Dose (mg/kg) | Compound I % Decrease | 13-cis retinoic acid % Decrease |
| 0.25 | −23 | −19 |
| 1.25 | −23 | −39 |
| 5 | −28 | −47 |

The following examples illustrate pharmaceutical preparations containing the compound of formula I as provided by the present invention.

EXAMPLE 5

Oral Solutions

| Ingredients | mg/mL |
|---|---|
| Formulation 1: | |
| Compound I | 50 mg |
| Ethanolamine | 15 mg |
| Alcohol, Anh. | 0.05 mL |
| Lecithin[1] | 50 mg |
| Glyceryl Monooleate | 0.1 mL |
| Polyglycolized apricot/kernel oil[2] q.s. to | 1.0 mL |
| Formulation 2: | |
| Compound I | 50 mg |
| Glyceryl Monooleate | 0.10 mL |
| 10% Sodium Hydroxide Solution in Alcohol | 0.05 mL |
| Polyethylene glycol 400 q.s. to | 1.0 mL |
| Formulation 3: | |
| Compound I | 50 |
| Butylated Hydroxyanisol | 1 |
| Medium Chain triglyceride q.s. to | 1 mL |
| Formulation 4: | |
| Compound I | 50 mg |
| Diethanolamine | 15 mg |
| Glycerin | 100 mg |
| Butylated Hydroxyanisol | 1 mg |
| Polyethylene glycol 400 q.s. to | 1 mL |
| Formulation 5: | |
| Compound I | 50 mg |
| Butylated Hydroxyanisol | 1 mg |
| Labrafil 1944 CS[2] q.s. to | 1 mL |

EXAMPLE 5

Capsule Formulations

| Ingredients | mg/cap | | |
|---|---|---|---|
| Compound I | 10 | 40 | 80 |
| Soybean Oil | 100.4 | 200.8 | 401.6 |
| Purified Beeswax | 7.5 | 15 | 30 |
| Hydrogenated Soybean Flakes | 7.5 | 15 | 30 |
| Hydrogenated Vegetable Oil | 26.5 | 53 | 106 |
| EDTA sodium | 0.5 | 1 | 2 |
| Butylated Hydroxy-anisol | 0.1 | 0.2 | 0.4 |
| | 162.5 | 325.0 | 650.0 |

Procedure: Heat Item 2 to about 70° C. and dissolve Item 2, 3, 4, 5 and 6 and mix until homogeneous solution is obtained. Cool to 30° C. Add Compound I and mix. Fill in soft shell capsule.

| Ingredients | mg/cap | | |
|---|---|---|---|
| Formulation 2: | | | |
| Compound I | 10 | 40 | 80 |
| Lactose Anhydrous | 50 | 95 | 190 |
| Corn Starch | 50 | 40 | 80 |
| Ascorbyl Palmitate | 2 | 5 | 10 |
| Talc | 10 | 20 | 40 |
| | 122 | 200 | 400 |

Procedure: Item 1, 2, 3, 4 and 5 were mixed and screened through #30 mesh screen. The screened powder mixture was remixed for 5 minutes and filled in appropriate capsule.

EXAMPLE 6

I.V. Solutions

| Ingredients | mg/mL |
|---|---|
| Formulation 1: | |
| Compound I | 10 mg |
| Alcohol, Anhydrous | 100 mg |
| Polyvinyl pyrolidone[3] (15 kDa) | 15 mg |
| Sodium Hydroxide 2N | 100 mg |
| Propylene glycol | 200 mg |
| Water for Injection Q.S | 1 mL |
| Formulation 2: | |
| Compound I | 10 mg |
| Benzyl Alcohol | 50 mg |
| Polyoxyethylene sorbitan monooleate[4] | 80 mg |
| Ethyl Alcohol | 100 mg |
| Polyethylene glycol 400 | 300 mg |
| Phosphate Buffer (pH 7.5) q.s. to | 1 mL |

[1]ALCOLEC 662, American Lecithin Co., New York, NY
[2]LABRAFIL 1944 CS, Gottefosse, Hawthorne, NY
[3]PVP K-15, BASF, Midland, MI
[4]TWEEN 80, ICI Corp., Wilmington, DE References Doran T. I., Baff R., Jacobs P., and Pacia E. Characterization of human sebaceous cells in Vitro. J. Invest. Dermatol. 96:341–348 (1991)

Farrell L. N., Strauss J. S., and Stranieri A. M. The treatment of severe cystic acne with 13-cis-retinoic acid. J. Amer. Acad. Dermatol. 3:602–611 (1980).

Hammerstein J., Meckies J., Leo-Rossberg I., Moltz L., and Zielske F. Use of cyproteron acetate in the treatment of acne, hirsutism and virilism. J. Steroid Biochem. 6:827–836 (1975).

Karasek M. Isolation and characterization of cells from the human sebaceous gland. In Vitro 22: Number 3, Part II, pg 22a, abstract #46 (1986).

Knutson D. D. Ultrastructral observations in acne vulgaris. The normal sebaceous follicles and acne lesions. J. Invest. Dermatol. 62:288–307 (1974).

Landthaler M., Kummermehr J., Wagner A., and Plewig G. Inhibitory effects of 13-cis-retinoic acid on human sebaceous glands. Arch. Dermatol. Res 269: 297–309 (1980).

Lavker R. M. and Leyden J. J. Lamellar inclusions in follicular horny cell: a new aspect of abnormal keratinization. J. Ultrastruc. Molec. Struct. Res. 69: 362–370 (1979).

Lavker R M, Leyden J. J., and McGinley K. J. The relationship between bacteria and the abnormal fillicular keratinization in acne vulgaris. J. Invest. Dermatol. 77: 325–330 ( 1981).

Lyons F., Marsden J. R., and Shuster S. Comparison of 13-cis-retinoic acid and cyproterone acetate on the clinical response, sebum secretion, dermal and epidermal lipogenesis in acne. Br. J. Dermatol. 106: 728–734 (1982).

Mezick J. A., Bhatia M. C., and Capetola R. J. Topical and systemic effects of retinoids on horn-filled utriculus size in the rhino mouse. A model to quantify "antikeratinizing" effects of retinoids. J. Invest. Dermatol. 83: 110–113 (1984).

Plewig G. and Luderschmidt C. Hamster ear model for sebaceous glands. J. Invest Dermatol. 68: 171–176 (1977).

Plewig G., Wagner A., Nikilowski J., and Landthaler M. Effects of two retinoids in animal experiments and after clinical application in acne patients: 13-cis-retinoic acid Ro 4-3780 and aromatic retinoid Ro 10-9359. In "Retinoids", CE Orfanos et al., ed., Springer-Verlag, p. 219–235, 1981.

Rheinwald J. G. and Green H. Serial cultivation of strains of human epidermal keratinocytes: The formation of keratinizing colonies from single cells. Cell 6: 331–334 (1975).

Shapiro S. S., Hurley J., Vane F. M., and Doran T. Evaluation of Potential Therapeutic Entities for the Treatment of Acne. In Reicherr U and Shoot B (eds): "Pharmacology of Retinoids in the Skin." Pharmacol. Skin., Basel, Karger, vol 3, pp 104–112 (1989).

Vane F. M., Bugge C. J. L., Rodriguez L. C., Rosenberger M., and Doran T. Human biliary metabolites of isotretinoin: Identification, quantitation, synthesis, and biological activity. Xenobiotica 20: 193–207 (1990).

Weissmann A., Bowden J., Frank B. L., Horwitz S. N., and Frost P. Antiandrogenic effects of topically applied spironolactone on the hamster flank organ. Arch. Dermatol. 121: 57–62 (1985).

Wolff H. H., Plewig G, and Braun-Falco O. Ultrastructure of human sebaceous sollicles and comedones following treatment with vitamin A. Acta. Derm. Vener. Stockh., Suppl. 74, pp 99–110 (1975).

We claim:

1. A method for treating acne which comprises the administration to patients of an effective amount of a composition comprising a therapeutically inert pharmaceutically acceptable carrier and a compound of the formula:

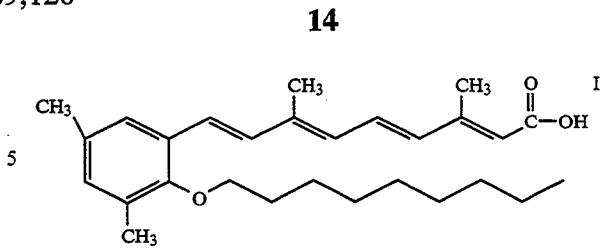

or its pharmaceutically acceptable salts or its pharmaceutically acceptable hydrolyzable esters.

2. A method in accordance with claim 1 wherein said composition is administered orally.

3. A method in accordance with claim 1 wherein said composition is administered topically.

4. A method for reducing sebum secretion which comprises the administration to patients of a composition containing a compound of the formula:

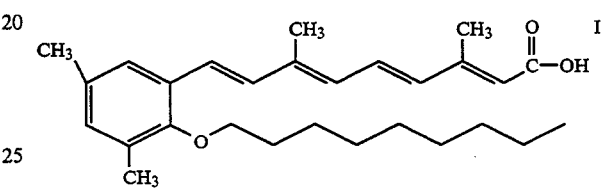

or its pharmaceutically acceptable salts or its pharmaceutically acceptable hydrolyzable esters, said composition being administered to provide said compound to said patients in an amount sufficient to reduce sebum secretion.

5. A method in accordance with claim 4 wherein said composition is administered orally.

6. A method in accordance with claim 5 wherein said composition is administered in the form of an oral pharmaceutical unit dosage, each unit dosage containing from about 1 mg to about 50 mg of said compound.

7. The method of claim 4, wherein said composition is administered topically.

8. The method of claim 7, wherein said composition is administered in a topical preparation, said preparation containing from at least 0.01 percent by weight to about 0.2 percent by weight of said compound.

* * * * *